(12) United States Patent
Roe

(10) Patent No.: US 8,684,951 B2
(45) Date of Patent: *Apr. 1, 2014

(54) BLOOD ACQUISITION SUSPENSION SYSTEM

(75) Inventor: Steven N. Roe, San Mateo, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 238 days.

This patent is subject to a terminal disclaimer.

(21) Appl. No.: 13/049,622

(22) Filed: Mar. 16, 2011

(65) Prior Publication Data

US 2011/0166477 A1 Jul. 7, 2011

Related U.S. Application Data

(60) Continuation of application No. 11/457,872, filed on Jul. 17, 2006, now Pat. No. 7,927,291, which is a division of application No. 10/737,660, filed on Dec. 16, 2003, now Pat. No. 7,351,212.

(60) Provisional application No. 60/436,952, filed on Dec. 30, 2002.

(51) Int. Cl.
*A61B 5/00* (2006.01)

(52) U.S. Cl.
USPC ........................................... 600/584

(58) Field of Classification Search
USPC ........... 600/584, 583, 576, 573; 606/181, 182
See application file for complete search history.

(56) References Cited

U.S. PATENT DOCUMENTS

| | | |
|---|---|---|
| 3,802,842 A | 4/1974 | Lange et al. |
| 3,854,471 A | 12/1974 | Wild |
| 4,061,468 A | 12/1977 | Lange et al. |
| 4,360,016 A | 11/1982 | Sarrine |
| 4,490,465 A | 12/1984 | Limbach et al. |
| 4,627,445 A | 12/1986 | Garcia et al. |
| 4,637,403 A | 1/1987 | Garcia et al. |
| 4,653,513 A | 3/1987 | Dombrowski |
| 4,787,398 A | 11/1988 | Garcia et al. |
| 4,869,249 A | 9/1989 | Crossman et al. |
| 4,924,879 A | 5/1990 | O'Brien |
| RE35,803 E | 5/1998 | Lange et al. |

(Continued)

FOREIGN PATENT DOCUMENTS

| | | |
|---|---|---|
| JP | H09-084781 | 9/1995 |
| JP | H10-014905 A | 1/1998 |

(Continued)

OTHER PUBLICATIONS

JP H10-14906 a Certified Translation.

*Primary Examiner* — Jeffrey G Hoekstra
*Assistant Examiner* — Fangemonique Smith
(74) *Attorney, Agent, or Firm* — Woodard, Emhardt, Moriarty, McNett & Henry LLP

(57) ABSTRACT

A body fluid sampling device includes a firing mechanism that is configured to be automatically cocked and fired. In one form, the device includes an electric motor that is operable to cock the firing mechanism and fire an integrated lancet/sampling device to form an incision in skin. Subsequent to formation of the incision, the integrated lancet device is temporarily removed from the skin to promote bleeding from the incision. After a specified period of time, the integrated lancet device is then repositioned against the skin in order to collect a fluid sample.

17 Claims, 3 Drawing Sheets

(56) References Cited

U.S. PATENT DOCUMENTS

| | | |
|---|---|---|
| 5,776,719 A | 7/1998 | Douglas et al. |
| 5,824,491 A | 10/1998 | Priest et al. |
| 5,857,983 A | 1/1999 | Douglas et al. |
| 5,873,887 A | 2/1999 | King et al. |
| 5,879,311 A | 3/1999 | Duchon et al. |
| 5,951,492 A | 9/1999 | Douglas et al. |
| 5,951,493 A | 9/1999 | Douglas et al. |
| 5,962,215 A | 10/1999 | Douglas et al. |
| 5,964,718 A | 10/1999 | Duchon et al. |
| 5,971,941 A | 10/1999 | Simons et al. |
| 6,048,352 A | 4/2000 | Douglas et al. |
| 6,056,701 A | 5/2000 | Duchon et al. |
| 6,056,765 A | 5/2000 | Bajaj et al. |
| 6,066,103 A | 5/2000 | Duchon et al. |
| 6,071,250 A | 6/2000 | Douglas et al. |
| 6,071,294 A | 6/2000 | Simons et al. |
| 6,086,545 A | 7/2000 | Roe et al. |
| 6,099,484 A | 8/2000 | Douglas et al. |
| 6,143,164 A | 11/2000 | Heller et al. |
| 6,159,424 A | 12/2000 | Kauhaniemi et al. |
| 6,183,489 B1 | 2/2001 | Douglas et al. |
| 6,210,420 B1 * | 4/2001 | Mauze et al. ............ 606/182 |
| 6,270,637 B1 | 8/2001 | Chrismore et al. |
| 6,306,104 B1 | 10/2001 | Cunningham et al. |
| 6,306,152 B1 | 10/2001 | Verdonk et al. |
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,352,514 B1 | 3/2002 | Douglas et al. |
| 6,561,989 B2 | 5/2003 | Whitson |
| 2002/0002344 A1 | 1/2002 | Douglas et al. |
| 2002/0018720 A1 | 2/2002 | Carlisle et al. |
| 2002/0029058 A1 | 3/2002 | Levaugn et al. |
| 2002/0082522 A1 | 6/2002 | Douglas et al. |
| 2002/0082632 A1 | 6/2002 | Spitz et al. |
| 2002/0103499 A1 | 8/2002 | Perez et al. |
| 2002/0169411 A1 | 11/2002 | Sherman et al. |
| 2002/0177763 A1 | 11/2002 | Burns et al. |
| 2002/0177788 A1 | 11/2002 | Hodges et al. |
| 2003/0060730 A1 | 3/2003 | Perez |
| 2003/0083686 A1 | 5/2003 | Freeman et al. |
| 2003/0144608 A1 | 7/2003 | Kojima et al. |
| 2004/0049219 A1 | 3/2004 | Briggs et al. |
| 2004/0087990 A1 | 5/2004 | Boecker et al. |
| 2004/0127818 A1 | 7/2004 | Roe |
| 2004/0138688 A1 | 7/2004 | Giraud |
| 2005/0049522 A1 | 3/2005 | Allen |

FOREIGN PATENT DOCUMENTS

| | | |
|---|---|---|
| WO | WO 93/09710 A1 | 5/1993 |
| WO | WO 01/72220 A1 | 10/2001 |
| WO | WO 02/46747 A1 | 6/2002 |
| WO | WO 02/100251 A2 | 12/2002 |
| WO | WO 2002/100460 A2 | 12/2002 |

* cited by examiner

BLOOD ACQUISITION SUSPENSION SYSTEM

REFERENCE TO RELATED APPLICATIONS

This application is a continuation of U.S. patent application Ser. No. 11/457,872, filed Jul. 17, 2006, now U.S. Pat. No. 7,927,291 which is a divisional of U.S. patent application Ser. No. 10/737,660, filed Dec. 16, 2003, now U.S. Pat. No. 7,351,212 which claims the benefit of U.S. Provisional Application No. 60/436,952, filed Dec. 30, 2002, all of which are hereby incorporated by reference in their entirety.

BACKGROUND OF THE INVENTION

The present invention generally relates to bodily fluid sampling devices and more specifically, but not exclusively, concerns an integrated body fluid sampling device that is adapted to temporarily remove and reapply the test strip to the incision site.

General Fluid Testing

The acquisition and testing of bodily fluids is useful for many purposes and continues to grow in importance for use in medical diagnosis and treatment and in other diverse applications. In the medical field, it is desirable for lay operators to perform tests routinely, quickly, and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

General Test Steps

The testing of bodily fluids basically involves the steps of obtaining the fluid sample, transferring the sample to a test device, conducting a test on the fluid sample, and displaying the results. These steps are generally performed by a plurality of separate instruments or devices.

Acquiring—Vascular

One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult, and is not advised for patients to perform on themselves.

Acquiring—Incising

The other common technique for collecting a bodily fluid sample is to form an incision in the skin to bring the fluid to the skin surface. A lancet, knife, or other cutting instrument is used to form the incision in the skin. The resulting blood or interstitial fluid specimen is then collected in a small tube or other container or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe, and the like, may be useful for sampling and are less painful. However, they also produce lesser amounts of blood. These alternate sites therefore are generally appropriate for use only for test systems requiring relatively small amounts of fluid or if steps are taken to facilitate the expression of the bodily fluid from the incision site.

Various methods and systems for incising the skin are known in the art. Exemplary lancing devices are shown, for example, in U.S. Pat. Nos. Re 35,803, issued to Lange, et al. on May 19, 1998; 4,924,879, issued to O'Brien on May 15, 1990; 5,879,311, issued to Duchon et al. on Mar. 9, 1999; 5,857,983, issued to Douglas et al. on Jan. 12, 1999; 6,183,489, issued to Douglas et al. on Feb. 6, 2001; 6,332,871, issued to Douglas et al. on Dec. 25, 2001; and 5,964,718, issued to Duchon et al. on Oct. 12, 1999. A representative commercial lancing device is the Accu-Chek Softclix® lancet.

Expressing

Patients are frequently advised to urge fluid to the incision site, such as by applying pressure to the area surrounding the incision to milk or pump the fluid from the incision. Mechanical devices are also known to facilitate the expression of bodily fluid from an incision. Such devices are shown, for example, in U.S. Pat. Nos. 5,879,311, issued to Duchon et al. on Mar. 9, 1999; 5,857,983, issued to Douglas et al. on Jan. 12, 1999; 6,183,489, issued to Douglas et al. on Feb. 6, 2001; 5,951,492, issued to Douglas et al. on Sep. 14, 1999; 5,951,493, issued to Douglas et al. on Sep. 14, 1999; 5,964,718, issued to Duchon et al. on Oct. 12, 1999; and 6,086,545, issued to Roe et al. on Jul. 11, 2000. A representative commercial product that promotes the expression of bodily fluid from an incision is the Amira AtLast® blood glucose system.

Sampling

The acquisition of the produced bodily fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision or is moved to the incision site shortly after the incision has been formed. A sampling tube may acquire the fluid by suction or by capillary action. Such sampling systems may include, for example, the systems shown in U.S. Pat. Nos. 6,048,352, issued to Douglas et al. on Apr. 11, 2000; 6,099,484, issued to Douglas et al. on Aug. 8, 2000; and 6,332,871, issued to Douglas et al. on Dec. 25, 2001. Examples of commercial sampling devices include the Roche Compact®, Amira AtLast®, Glucometer Elite®, and Therasense FreeStyle® test strips.

Testing General

The bodily fluid sample may be analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Examples of such test systems include those in U.S. Pat. Nos. 5,824,491, issued to Priest et al. on Oct. 20, 1998; 5,962,215, issued to Douglas et al. on Oct. 5, 1999; and 5,776,719, issued to Douglas et al. on Jul. 7, 1998.

Typically, a test system takes advantage of a reaction between the bodily fluid to be tested and a reagent present in the test system. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

Blood Glucose

A common medical test is the measurement of blood glucose level. The glucose level can be determined directly by analysis of the blood or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise, and other factors.

In testing for the presence of an analyte such as glucose in a bodily fluid, test systems are commonly used which take advantage of an oxidation/reduction reaction which occurs using an oxidase/peroxidase detection chemistry. The test reagent is exposed to a sample of the bodily fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength or a blood glucose meter. Electrochemical and other systems are also well known for testing bodily fluids for properties on constituents.

Testing Difficulties

Performing the above-discussed steps can be difficult for patients, especially for patients with limited hand dexterity, such as the elderly. Typical lancing devices require the user to manually cock the lancet. As should be appreciated, manual cocking of the device may be difficult for those with hand dexterity problems. In a typical procedure, after cocking the firing mechanism, the patient fires the lancet at the skin in order to form an incision in the skin. Once a sufficient amount of fluid collects as a droplet from the incision in the skin, the patient has to position a test strip over the incision site such that the test strip contacts and absorbs a sufficient amount of the fluid for testing. Usually, these droplets of fluid are quite small, and patients, especially ones with poor hand motor control, may experience great difficulty in positioning the test strip so as to collect an adequate sample from an individual droplet. As should be appreciated, a patient can become quickly frustrated by this procedure and, consequently, they may perform the test less often or may even quit testing altogether. Moreover, the pressure applied against the skin by the test strip during sampling can cause the incision to close, thereby prematurely cutting off the fluid supply. If the fluid supply from the incision is cut off too soon, an insufficient amount of the fluid may be collected on the test strip for testing.

Thus, needs remain for further contributions in this area of technology.

SUMMARY OF THE INVENTION

One aspect the present invention concerns a bodily fluid sampling device that temporarily removes a fluid collection means from skin so as to promote fluid formation from an incision in the skin.

Another aspect concerns a method for sampling bodily fluid. The method includes forming an incision in the skin with an integrated lancet/sampling device. The device is temporarily withdrawn from the skin to promote fluid formation from the incision. The device is then reapplied proximal to the fluid or in contact with the skin in order to collect the fluid.

Still yet another aspect concerns a bodily fluid sampling device able to automatically cock a firing mechanism before lancing the skin.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
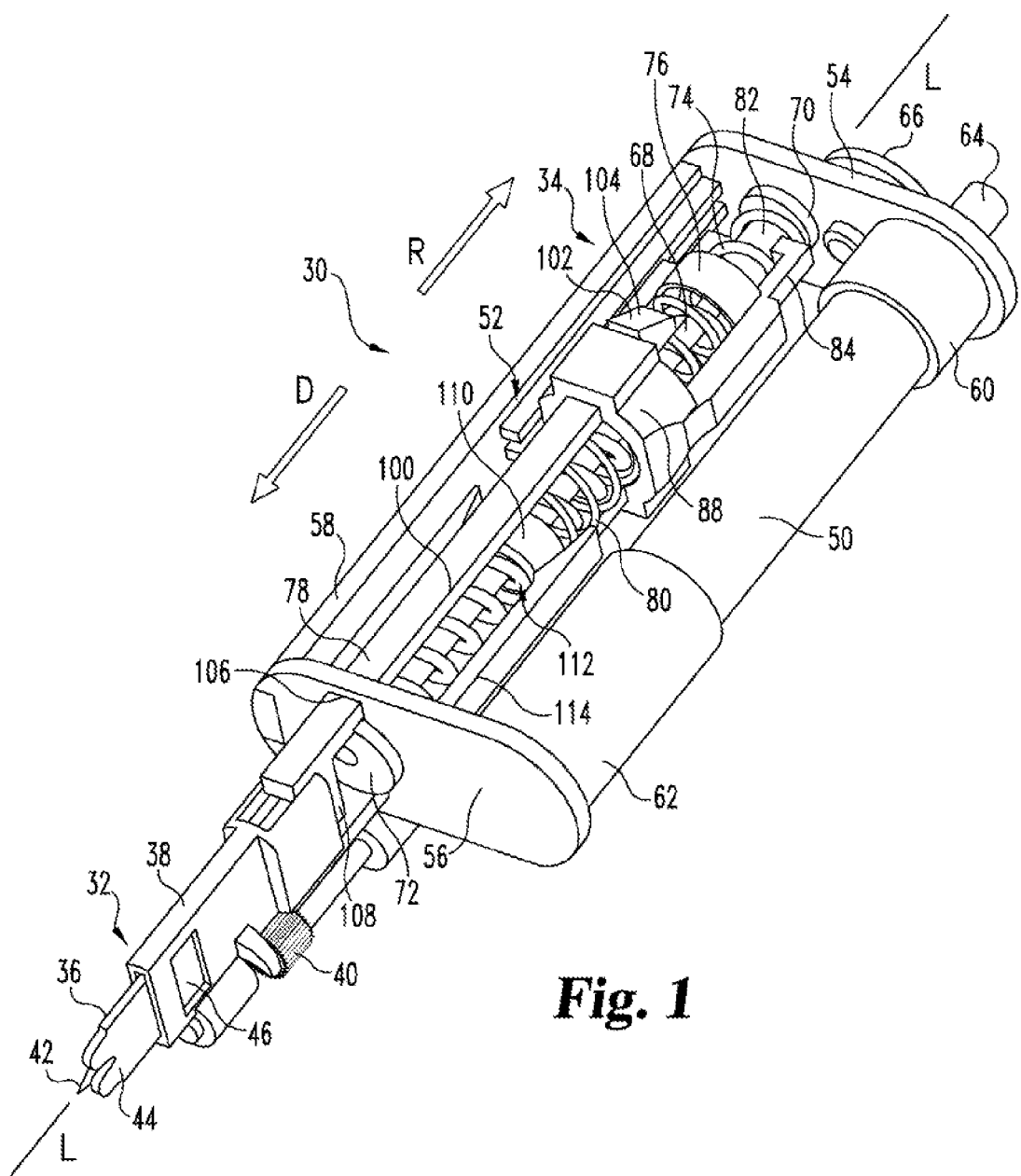
FIG. 1 is a perspective view of a bodily fluid sampling device according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention generally concerns an integrated skin lancing device that reduces the number of steps involved in forming, collecting, and testing a bodily fluid sample from an incision. More specifically, the device is operable to automatically cock the lancing mechanism, and the device is further operable to temporarily lift the device from contact with the skin and reposition the device over the incision site in order to collect a fluid sample. By temporarily lifting the device from the skin, no pressure is applied to the skin by the device, which could potentially close the incision and limit the fluid supply for the sample. In one embodiment, the device includes an electric motor that automatically cocks the lancing mechanism and temporarily lifts a fluid collection means from the skin. It is contemplated that, in another embodiment, a purely mechanical system can be used to temporarily lift the fluid collection means.

An integrated bodily fluid sampling device 30 according to one embodiment, among others, of the present invention will now be described with reference to FIGS. 1-2. As depicted in FIG. 1, device 30 includes a sampling end portion 32 and an actuation end portion 34. The sampling end portion 32 includes an integrated lancet/sampling device 36, a holder 38 for device 36, and a depth control mechanism 40. Device 36 is configured to lance an incision into the skin, collect a bodily fluid sample from the incision, and analyze the fluid sample. In device 36, a lancet or blade 42 for forming the incision is housed in a casing 44. For illustration purposes, so that the lancet 42 can be seen in FIG. 1, lancet 42 is shown in an extended state. Normally, when the lancet 42 is not lancing the skin, the lancet 42 is retracted inside the casing 44. During lancing, the casing 44 is pressed against the skin to form a reference surface on which the penetration depth of the lancet 42 is based. As device 36 is further pressed against the skin, the casing 44 slides relative to the lancet 42 such that the lancet 42 is exposed, thereby lancing the incision into the skin. Device 36 further includes a test strip or media 46 for analyzing the fluid sample. The test strip 46 can analyze fluid through such means as optical (e.g., reflectance, absorption, fluorescence, Raman, etc.), electrochemical, and/or magnetic analysis, to name a few. In one embodiment, the test strip analyzes fluid optically through a chemical reagent. A capillary channel is formed between the casing 44 and the lancet 42, which draws fluid onto the test strip 46 via capillary action. As previously mentioned, the holder 38 holds device 36 during lancing. The depth control mechanism 40 is used to control and change the penetration depth of the lancet 42 into the skin. For a further discussion of these components in the sampling end portion 32 as well as their function, please refer to commonly owned U.S. patent application Ser. No. 10/330, 724 entitled "PRECISION DEPTH CONTROL LANCING TIP", filed on Dec. 27, 2002, which is hereby incorporated by reference in its entirety. As will be appreciated from the discussion below, the bodily fluid sampling device 30 according to the present invention can be modified to be used in conjunction with other types of lancing and/or sampling devices.

Figure 2:
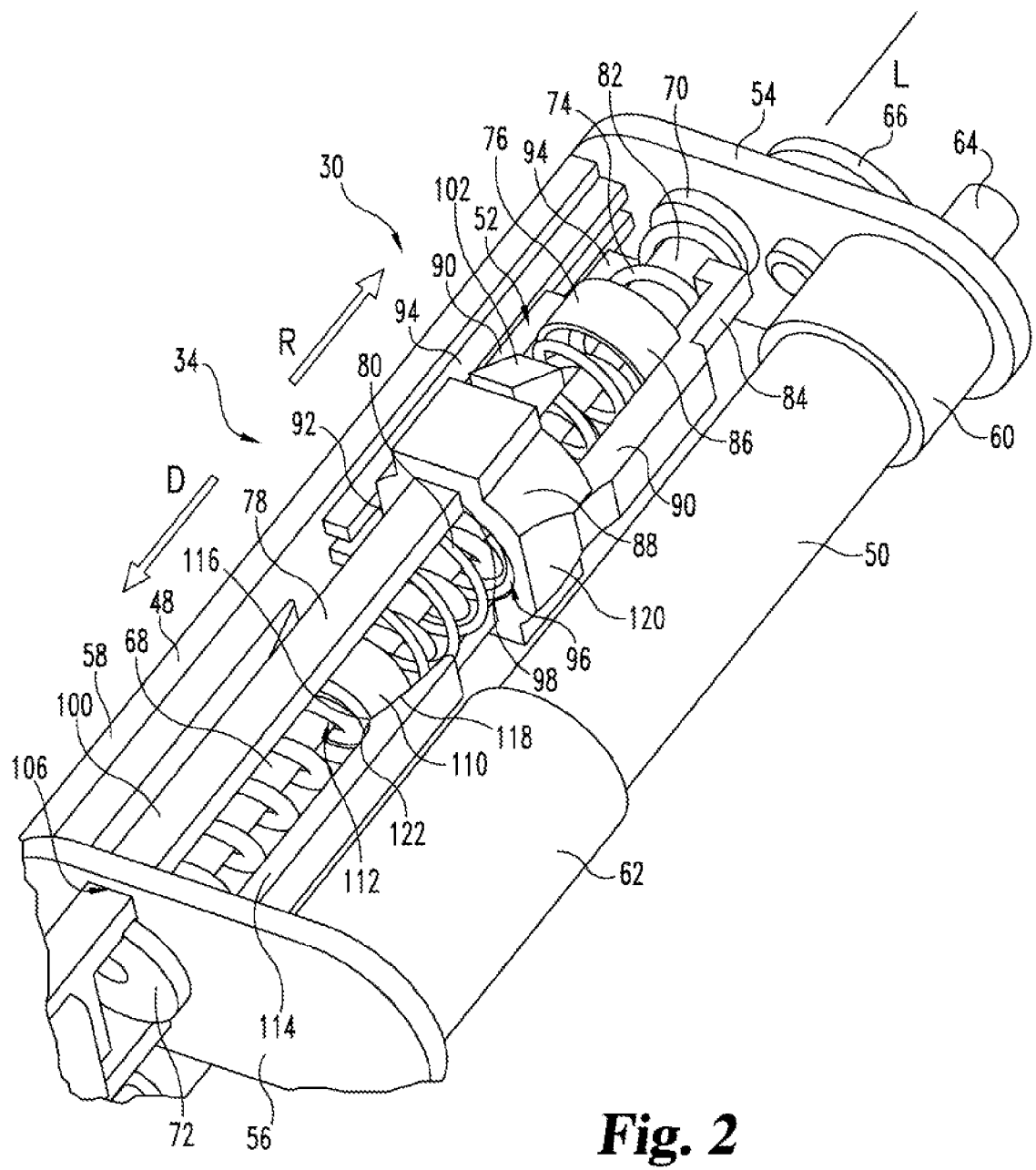
FIG. 2 is an enlarged, perspective view of the FIG. 1 device.

FIG. 2 illustrates an enlarged view of the actuation portion 34 of the sampling device 30. So that the actuation portion 34 can be easily viewed, FIGS. 1 and 2 show the device 30 without a housing. However, it should be appreciated that device 30 can include a housing in order to protect the components of device 30 from the outside environment. As shown, the actuation portion 34 includes a support structure 48 that supports a motor 50 as well as a firing mechanism 52. The firing mechanism 52 is used to fire the integrated lancet/sampling device 36 in order to lance the skin, and the motor 50 is used to cock the firing mechanism 52 as well as to temporarily retract device 36 after lancing. The support structure 48 in the illustrated embodiment has first 54 and second 56 support arms that are connected together through an actuation guide member 58 such that support structure 48 is shaped in the form of a "C". Opposite guide member 58, the first 54 and second 56 support arms respectively have first 60 and second 62 motor mounts in which the motor 50 is mounted. The illustrated motor 50 has a generally cylindrical shape, but it is contemplated that motor 50 can have other shapes. As illustrated, motor mounts 60 and 62 each have a hollow cylindrical shape so as to coincide with the cylindrical shape of the motor 50 such that motor 50 is able to fit inside mounts 60 and 62. However, it should be appreciated that motor mounts 60 and 62 can be shaped differently so as to coincide with the shape of differently shaped motors.

In the illustrated embodiment, the motor 50 includes a reversible electric motor, but it should be appreciated that motor 50 can include other types of motors, such as a pneumatic motor. Moreover, in another embodiment in which the motor 50 is non-reversible, the device 30 can include a transmission configured to reverse the outputted force from the motor 50. In one embodiment, the motor 50 is powered by an internal power source, such as a battery or a fuel cell, but it is contemplated that the motor 50 can be powered in other manners, such as externally through an electrical outlet. As depicted in FIGS. 1 and 2, the motor 50 has a drive shaft with a drive gear 64 that extends through the first support arm 54. A reduction gear 66, which is rotatably mounted to the first support arm 54, operatively engages the drive gear 64 of the motor 50. The firing mechanism 52 includes a guide rod 68 that extends between the first 54 and second 56 support arms along longitudinal axis L of the device 30. As illustrated, the guide rod 68 is rotatably mounted to the first 54 and second 56 support arms via first 70 and second 72 bushings, respectively. At the first support arm 54, the guide rod 68 operatively engages the reduction gear 66 such that the motor 50 is able to rotate the guide rod 68. A drive thread or coil 74, which winds in a helical pattern around the guide rod 68, is attached to the guide rod 68 at both ends through bushings 70 and 72 in one embodiment. In another embodiment, the ends of the drive thread 74 are directly attached to the guide rod 68. As noted above, the guide rod 68 is operatively engaged to the motor 50 via the reduction gear 66. Both the guide rod 68 and the drive thread 74, in the illustrated embodiment, rotate in unison as the motor 50 rotates the reduction gear 66. It is contemplated that in another embodiment only the drive thread 74 operatively engages the reduction gear 66 such that the guide rod 68 remains stationary as the drive thread 74 rotates.

Referring to FIG. 2, the firing mechanism 52 further includes a drive member 76 that engages the drive thread 74 and an actuation member 78 that is coupled to holder 38. A spring (or elastic means) 80 is coupled between the drive member 76 and the actuation member 78. Among its many functions, the spring 80 is used to fire the lancet 42 from device 36. During cocking, the motor 50 via drive thread 74 drives the drive member 76 towards the actuation member 78 such that the spring 80 is compressed therebetween. As will be described in greater detail below, the potential energy stored by the compressed spring 80 is then used to fire the actuation member 78, which in turn extends the lancet 42 from the integrated lancet/sampling device 36.

As depicted, the drive member 76 has a rod engagement portion 82 that is slidably received along the guide rod 68. In FIG. 2, the rod engagement portion 82 is positioned inside the drive thread 74 and has one or more thread engaging arms 84 extending therefrom that engage the drive thread 74. In the illustrated embodiment, the rod engagement portion 82 has a pair of L-shaped thread engaging arms 84 positioned on opposite sides of the rod engagement portion 82, and the thread engaging arms 84 extend through the drive thread 74. It should be appreciated that the rod engagement portion can include more or less thread engaging arms 84 than is shown. Through the engagement between the drive thread 74 and the thread engaging arms 84, the motor 50 is able to move the drive member 76 along longitudinal axis L in either a driving direction D or a retraction direction R. For example, rotating the drive thread 74 in a clockwise fashion moves the drive member 76 in direction D, and rotating the drive thread 74 in a counterclockwise fashion moves the drive member 76 in direction R. It should be appreciated, however, that the drive thread 74 in other embodiments can be coiled in an opposite fashion such that the drive thread 74 can be rotated in clockwise direction to move the drive member 76 in direction R and counterclockwise to move the drive member 76 in direction D.

The drive member 76 further includes a spring engagement portion 86 and an actuation member engagement portion 88. As shown, the spring 80 is attached to the spring engagement portion 86, and the thread engaging arms 84 attach the rod engagement portion 82 to the spring engagement portion 86. In the illustrated embodiment, the spring engagement portion 86 is ring shaped so as to fit around the drive thread 74. One or more guide arms 90 connect the spring engagement portion 86 to the actuation member engagement portion 88. As shown, the drive member 76 in the illustrated embodiment has a pair of guide arms 90 that are disposed on opposite sides of the drive member 76. At least one of the guide arms 90 is constructed to include a guide tab 92 that is slidably received between a pair of guide rails 94 that extend from the guide member 58 of the support structure 48. It, however, should be understood that device 30 can include more or less guide arms 90 and guide rails 94 than is shown. The guide rails 94 in conjunction with the guide tab 92 direct the drive member 76 to move along the longitudinal axis L and prevent the drive member 76 from rotating in response to the rotation of the drive thread 74. Referring to FIG. 2, portion 88 of the drive member 76 defines a spring opening 96 through which the spring 80, the drive thread 74, and the guide rod 68 extend. Around opening 96 the drive member 76 defines one or more engagement notches 98 in which the actuation member 78 is slidably received.

With reference to FIG. 1, the actuation member 78 includes one or more (and in the illustrated embodiment a pair of) slide arms 100 that are slidably received in the engagement notches 98 defined in the drive member 76. Each of the slide arms 100 has a stop tab 102 located at the end proximal the drive member 76. As shown, the stop tab 102 has a beveled insertion surface 104 that aids in slidably attaching the actuation member 78 to portion 88 of the drive member 76. At the second support arm 56, the slide arms 100 extend through slide arm openings 106 that are defined in the second support arm 56 such that the slide arms 100 are able to move in a sliding fashion through openings 106. The ends of the slide arms 100 that are connected to the holder 38 are connected together via a connection member 108. In the support structure 48, the slide arms 100 are connected to together through a cocking flange 110. In the illustrated embodiment, the cocking flange 110 is ring shaped and defines a thread opening 112 through which the drive thread 74 extends.

As shown in FIG. 2, the spring 80 is attached to the cocking flange 110 such that the spring 80 is coupled between the spring engagement portion 86 of the drive member 76 and the cocking flange 110 of the actuation member 78. During cocking of the device 30, the motor 50 rotates the drive thread 74 so that the drive member 76 is driven toward the cocking flange 110 of the actuation member 78. As the drive member 76 is driven towards flange 110, a pair of cocking arms 114, which extend from the second support arm 56 in a parallel arrangement with respect to the longitudinal axis L, support the cocking flange 110 against the force applied by the spring 80. It should be appreciated that device 30 in other embodiments can include one or more cocking arms 114. The cocking arms 114 have support tabs 116 that face one another in order to support the cocking flange 110 during cocking. Proximal the drive member 76, the cocking arms 114 have drive member engagement surfaces 118 with an angled or beveled shape. Similarly, the drive member 76 has cocking arm engagement surfaces 120 that are likewise beveled or angled to coincide with the shape of the drive member engagement surfaces 118. As the drive member 76 is driven towards the cocking arms 114 during cocking, the cocking arm engagement surfaces 120 spread the cocking arms 114 apart such that the cocking flange 110 is released. Upon flange 110 being released, the compressed spring 80 drives the cocking flange 110 away from the drive member 76, thereby driving the integrated lancet/sampling device 36 to lance the skin. As depicted in FIG. 2, the cocking arms 114 further have reengagement surfaces 122 that are angled in order to allow the cocking flange 110 to reengage the support tabs 116.

Figure 3:
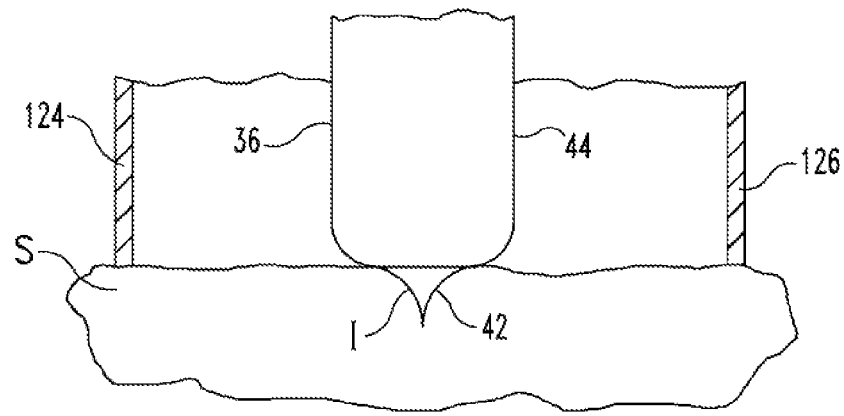
FIG. 3 is a cross sectional view of the FIG. 1 device forming an incision into skin.
Figure 4:
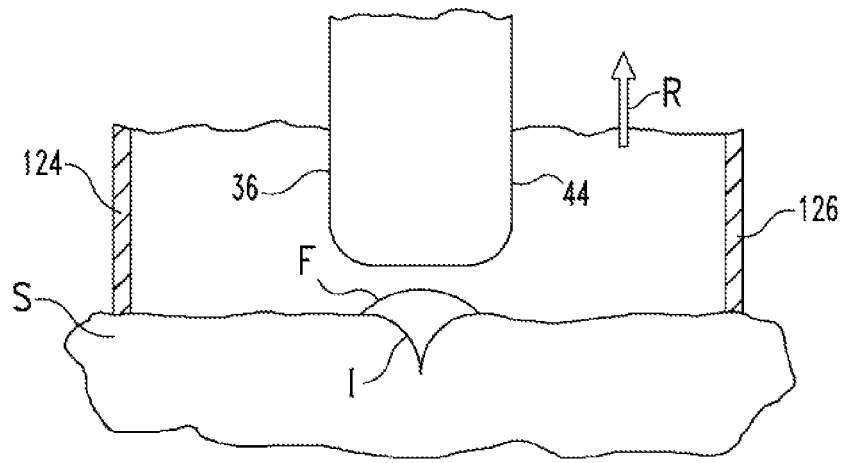
FIG. 4 is a cross sectional view of the FIG. 1 device temporarily retracted from the skin.
Figure 5:
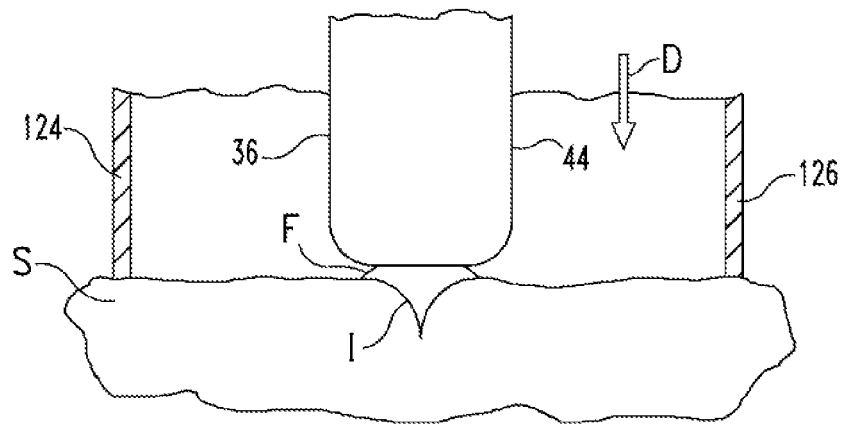
FIG. 5 is a cross sectional view of the FIG. 1 device configured to collect fluid from the incision.

The operation of the integrated bodily fluid sampling device 30 according to one embodiment will now be described with reference to FIGS. 1, 2, 3, 4, and 5. FIGS. 3, 4, and 5 illustrate the relative position of the sampling device 36 in relation to skin S during the sampling technique according to one embodiment of the present invention. In the illustrated embodiment, device 30 has a housing 124 that is coupled to the support structure 48, and as shown, the housing 124 includes a skin contact portion 126, which surrounds the sampling device 36, so as to position device 30 with the skin S. In one form, the skin contact portion 126 is cylindrical in shape, but it is should be appreciated that the skin contact portion 126 can be shaped differently. Moreover, it is contemplated that in other embodiments the skin contact portion 126 can be entirely or partially omitted such that the person using the fluid sampling device 30 manually holds device 30 in position over the skin S. The skin contact portion 126 in the illustrated embodiment is sized so as to not to apply force to the skin that can close incision I once formed.

Initially, the cocking flange 110 of the firing mechanism 52 engages the support tabs 116 of the cocking arms 114, as is shown in FIG. 1. In on order to initiate lancing, the user positions device 36 either in contact with or proximal to the skin S. In the embodiment illustrated in FIG. 3, the user presses the skin contact portion 126 against the skin S so as to position device 36. To cock the firing mechanism 52, as depicted in FIG. 2, the motor 50 via reduction gear 66 rotates the drive thread 74 so that the drive member 76 is driven in driving direction D along longitudinal axis L towards the cocking flange 110 of the actuation member 78. Cocking can be initiated by the user through a switch on device 30 that activates the motor 50 and/or automatically through a controller in the device 30. It should be appreciated that the motor 50 can be activated in other manners. Since the cocking flange 110 is engaged with the cocking arms 114, the spring 80 in the firing mechanism 52 becomes compressed as the drive member 76 is driven in direction D. When the drive member 76 is further driven in direction D, the stop tabs 102 of the actuation member 78 disengage from the actuation member engagement portion 88 of the drive member 76 such that the slide arms 100 slide within the engagement openings 98 of the drive member 76. Eventually, as the spring 80 becomes further compressed by the drive member 76, the arm engagement surfaces 120 on the drive member 76 engage the drive member engagement surfaces 118 on the cocking arms 114 such that the cocking arms 114 are pried apart from one another. Once arms 114 are sufficiently bent away from one another, the support tabs 116 on the cocking arms 114 disengage from the cocking flange 110.

As soon as the cocking flange 110 is disengaged, the compressed spring 80 expands so as to drive the actuation member 78 in direction D towards the skin. After the firing mechanism 52 is fired, the motor 50 in one embodiment stops driving the drive member 76. In one form, a timer is used to control the operation of the motor 50. Nevertheless, it is contemplated that the motor 50 can be controlled in other manners, such as through a controller and sensors. When the actuation member 78 is fired, the actuation member 78 presses the casing 44 of the integrated lancet/sampling device 36 against the skin, and the lancet 42 inside the casing 44 slides relative to the casing 44 so as to extend from the casing 44, thereby lancing the incision I in the skin S (FIG. 3). The depth control mechanism 40 controls the penetration depth of the lancet 42. Once the incision of the proper depth is formed, a retraction mechanism, such as a leaf spring in device 36, retracts the lancet 42 back inside the casing 44. In addition, the forward progression of the actuation member 78 in direction D is stopped in one embodiment by the stop tabs 102 contacting the actuation member engagement portion 88 on the drive member 76. In another embodiment, the movement of the actuation member 78 is stopped by the cocking flange 110 hitting the second support arm 56.

To prevent the pressure applied by the casing 44 from prematurely closing the incision, thereby limiting the fluid supplied from the incision, the bodily fluid sampling device 30 according to one embodiment of the present invention temporarily lifts the integrated lancet/sampling device 36 in direction R from the skin, as is shown in FIG. 4. Afterwards, the bodily fluid sampling device 30 reapplies the casing 44 of device 36 against the skin or positions device 36 proximal the skin such that the integrated lancet/sampling device 36 is able to collect a fluid sample from the incision, as is illustrated in FIG. 5. As should be appreciated, this sampling technique according to the present invention increases the size of the fluid sample by not restricting the fluid flow from the incision I. In one embodiment, the bodily fluid sampling device 30 lifts the integrated lancet/sampling device 36 for two (2) seconds before reapplying device 36 against the skin. However, it should be appreciated that device 36 can be temporarily lifted from the skin for different time intervals. To temporarily remove device 36 from the skin S, the motor 50 in FIG. 2 is reversed such that the drive thread 74 is rotated in an opposite direction (as compared to when cocking the firing mechanism), thereby moving the drive member 76 in retraction direction R. For example, the drive thread 74 can be rotated in a clockwise direction to move drive member 76 in direction D and can be rotated in a counterclockwise direction so as to move the drive member 76 in direction R. As should be appreciated, the drive member 76 in other embodiments can be advanced in direction D and retracted in direction R by rotating the drive thread 74 in an opposite fashion. While the drive member 76 is driven in direction R, the stop tabs 102, which engage the drive member 76, also pull the actuation member 78 in direction R. When the actuation member 78 is moved in direction R, device 36 is likewise moved in direction R, thereby lifting the casing 44 of device 36 from the skin S (FIG. 4). In one embodiment, the integrated lancet/sampling device 36 is lifted a small distance from the skin, and in particular, device 36 is lifted 1 mm from the skin. It should be appreciated, however, that device 36 can be retracted at different distances from the skin.

Once device 36 has been lifted from the skin for a short period of time, the motor 50 is then again reversed so as to drive the drive member 76 in direction D. The force applied by the drive member 76 against the spring 80 is transferred to the actuation member 78 so that device 36 is moved in direction D towards the skin (FIG. 5). When the integrated lancet/sampling device 36 contacts the skin S or is positioned at the desired distance from the skin S, the motor 50 can be deenergized. The bodily fluid F that has formed as a droplet from the incision I in the skin S is drawn via capillary action into the capillary cavity formed in the casing 44 and deposited onto the test strip 46 in device 36 so that the fluid sample can be analyzed.

To reset the bodily fluid sampling device 30 for future sample collection, the motor 50 drives the drive member 76 in the retraction direction R such that the actuation mechanism 78 is likewise pulled in the retraction direction R. As the actuation mechanism 78 is pulled in direction R, the cocking flange 110 engages the reengagement surfaces 122 on the cocking arms 114, and the arms 114 are pried apart so that the cocking flange 110 reengages the support tabs 116 on the cocking arms 114. Once the bodily fluid sampling device 30 is reset, the firing mechanism 52 can be again cocked and fired in the manner as described above.

It is contemplated that, in another embodiment, a purely mechanical device can be used to accomplish the sampling technique as described above in which the integrated lancet/sampling device is temporarily removed and reapplied to the skin. In one form, a hydraulic and/or pneumatic cylinder is used to dampen or slow the mechanical movement in which the integrated lancet/sampling device is temporarily removed and reapplied.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A body fluid sampling device, comprising:
   a housing configured to contact tissue;
   an integrated lancing-sampling device including a casing and a lancet for lancing an incision in the tissue slidably received in the casing, wherein the casing defines a sampling cavity for drawing body fluid from the incision, wherein the integrated lancing-sampling device is disposed inside the housing, wherein the casing of the integrated lancing-sampling device forms a reference surface upon which penetration depth of the lancet is based when the casing is pressed against the tissue, wherein the casing and the lancet of the lancing-sampling device are configured to be removed from the housing as a single disposable unit; and
   a positioner mechanism configured to retract the casing of the integrated lancing-sampling device from contact with the tissue after cutting the incision to a retracted position to promote flow of body fluid from the incision while the housing remains in contact with the tissue, the positioner mechanism being configured to subsequently move the integrated lancing-sampling device from the retracted position to a collection position where the body fluid is collected, wherein the casing of the integrated lancing-sampling device is positioned closer to the tissue at the collection position than at the retracted position.

2. The device of claim 1, further comprising a firing mechanism coupled to the integrated lancing-sampling device for firing the integrated lancing-sampling device.

3. The device of claim 2, further comprising:
   wherein the firing mechanism includes a spring configured to fire the lancet; and
   means for automatically cocking the spring of the firing mechanism.

4. The device of claim 3, further comprising:
   wherein the means for automatically cocking the spring of the firing mechanism includes a motor; and
   the firing mechanism including
      a holder in which the integrated lancing-sampling device is received,
      a guide rod operatively engaged with the motor, the guide rod including a drive thread winding in a helical pattern around the guide rod,
      a drive member engaging the drive thread,
      an actuation member coupled to the holder, the actuation member including one or more slide arms slidably attaching the actuation member to the drive member and a cocking flange coupled to the slide arms,
      one or more cocking arms engageable with the cocking flange to hold the actuation member in place during cocking,
      the spring being coupled between the drive member and the actuation member, wherein the spring is configured to be compressed between the drive member and the actuation member as the motor drives the drive member towards the actuation member via the drive thread on the guide rod, and
      wherein the drive member includes one or more arm engagement surfaces configured to release the cocking flange from the cocking arms to fire the lancet via the spring.

5. The device of claim 4, wherein the motor includes a reversible motor with a drive shaft configured to rotate in a first direction during retraction of the integrated lancing-sampling device and in a second direction during extension of the integrated lancing-sampling device.

6. The device of claim 1, further comprising a depth control mechanism coupled to the integrated lancing-sampling device to adjust the penetration depth of the lancet.

7. The device of claim 1, wherein the integrated lancing-sampling device includes a spring to retract the lancet from the incision.

8. The device of claim 1, wherein the integrated lancing-sampling device includes a reference surface against which the tissue is pressed during lancing to control penetration depth of the lancet.

9. The device of claim 1, wherein the positioner mechanism includes:
- a reversible motor with a drive shaft configured to rotate in a first direction during retraction of the integrated lancing-sampling device and in a second direction during extension of the integrated lancing-sampling device, the drive shaft including a drive thread winding in a helical pattern around the drive shaft;
- a holder in which the integrated lancing-sampling device is received;
- a drive member engaging the drive thread;
- an actuation member coupled to the holder, the actuation member including one or more slide arms slidably attaching the actuation member to the drive member and a cocking flange coupled to the slide arms;
- one or more cocking arms engageable with the cocking flange to hold the actuation member in place during cocking; and
- a spring coupled between the drive member and the actuation member, wherein the spring is configured to be compressed between the drive member and the actuation member as the motor drives the drive member towards the actuation member via the drive thread on the drive shaft.

10. A body fluid sampling device, comprising:
- an integrated lancing-sampling device including a lancet configured to lance an incision in tissue;
- a firing mechanism coupled to the integrated lancing-sampling device, the firing mechanism including a spring configured to fire the lancet;
- a cocking mechanism coupled to the spring configured to place the spring in a cocked state, wherein the cocking mechanism includes an electric motor configured to deform the spring for storing potential energy in the spring when in the cocked state;
- wherein the integrated lancing-sampling device includes a casing;
- wherein the motor is configured to retract the integrated lancing-sampling device from contact with the tissue after cutting the incision and subsequently move the integrated lancing-sampling device to a collection position where the body fluid is collected; and
- wherein the casing of the integrated lancing-sampling device is located closer to the tissue at the collection position than when retracted.

11. The device of claim 10, wherein the firing mechanism includes:
- a holder in which the integrated lancing-sampling device is received;
- a guide rod operatively engaged with the motor, the guide rod including a drive thread winding in a helical pattern around the guide rod;
- a drive member engaging the drive thread;
- an actuation member coupled to the holder, the actuation member including one or more slide arms slidably attaching the actuation member to the drive member and a cocking flange coupled to the slide arms;
- one or more cocking arms engageable with the cocking flange to hold the actuation member in place during cocking;
- a spring coupled between the drive member and the actuation member, wherein the spring is configured to be compressed between the drive member and the actuation member as the motor drives the drive member towards the actuation member via the drive thread on the guide rod; and
- wherein the drive member includes one or more arm engagement surfaces configured to release the cocking flange from the cocking arms to fire the lancet via the spring.

12. The device of claim 10, wherein the motor includes a reversible motor with a drive shaft configured to rotate in a first direction during retraction of the integrated lancing-sampling device and in a second direction during extension of the integrated lancing-sampling device.

13. A method, comprising:
- placing a housing of a body fluid sampling device against tissue;
- lancing tissue by firing a lancet of an integrated lancing-sampling device while the housing remains in contact with the tissue, wherein the lancet of the integrated lancing-sampling device is slidably received in a casing, wherein the casing contacts the tissue during said lancing, wherein the casing defines a sampling cavity for drawing body fluid from an incision;
- retracting the casing of the integrated lancing-sampling device from contact with the tissue to a retracted position to promote flow of body fluid from the incision after said lancing, wherein the housing remains in contact with the tissue during said retracting;
- moving the integrated lancing-sampling device from the retracted position to a collection position after said retracting the casing, wherein the housing remains in contact with the tissue during said moving, wherein the casing of the integrated lancing-sampling device is located closer to the tissue at the collection position than at the retracted position; and
- collecting the body fluid by drawing the body fluid from the incision into the sampling cavity of the casing while the housing remains in contact with the tissue.

14. The method of claim 13, further comprising:
- wherein the body fluid sampling device includes a reversible motor with a drive shaft, wherein the drive shaft includes a drive thread winding in a helical pattern around the drive shaft;
- rotating the drive shaft in a first direction during said retracting; and
- rotating the drive shaft in a second direction during said moving the integrated lancing-sampling device.

15. The method of claim 13, further comprising:
- wherein the body fluid sampling device includes
  - a motor,
  - a holder in which the integrated lancing-sampling device is received,
  - a guide rod operatively engaged with the motor, the guide rod including a drive thread winding in a helical pattern around the guide rod,
  - a drive member engaging the drive thread, an actuation member coupled to the holder, the actuation member including one or more slide arms slidably attaching the actuation member to the drive member and a cocking flange coupled to the slide arms, one or more cocking arms engageable with the cocking flange to hold the actuation member in place during cocking, and a spring coupled between the drive member and the actuation member, wherein the spring is configured to be compressed between the drive member and the actuation member as the motor drives the drive member towards the actuation member via the drive thread on the guide rod, and wherein said lancing the tissue includes cocking the spring by compressing the spring between the drive member and the actuation member with the motor at least until the cocking flange engages the cocking arms to hold the spring in a cocked state, and releasing the spring by driving one or more arm engagement surfaces of the drive member with the motor to release the cocking flange from the cocking arms.

16. A method, comprising:

cocking a firing mechanism to a cocked state by compressing a spring of the firing mechanism with an electric motor;

firing a lancet with the firing mechanism by releasing the spring from the cocked state;

wherein the lancet is incorporated into an integrated lancing-sampling device in which the lancet is slidably received in a casing of the integrated lancing-sampling device, wherein the casing defines a sampling cavity for drawing body fluid from an incision;

drawing the body fluid from the incision into the sampling cavity of the integrated lancing-sampling device;

further comprising placing a housing of a body fluid sampling device against tissue, wherein the body fluid sampling device includes the firing mechanism;

keeping the housing in contact with the tissue during said firing;

retracting the casing of the integrated lancing-sampling device from contact with the tissue to a retracted position to promote flow of body fluid from the incision after said firing, wherein the housing remains in contact with the tissue during said retracting; and moving the integrated lancing-sampling device from the retracted position to a collection position after said retracting the casing, wherein the housing remains in contact with the tissue during said moving.

17. The method of claim 16, further comprising:

wherein the firing mechanism includes a holder in which the lancet is received, a guide rod operatively engaged with the motor, the guide rod including a drive thread winding in a helical pattern around the guide rod, a drive member engaging the drive thread, an actuation member coupled to the holder, the actuation member including one or more slide arms slidably attaching the actuation member to the drive member and a cocking flange coupled to the slide arms, one or more cocking arms engageable with the cocking flange to hold the actuation member in place during said cocking, and the spring coupled between the drive member and the actuation member, wherein the spring is configured to be compressed between the drive member and the actuation member as the motor drives the drive member towards the actuation member via the drive thread on the guide rod, and wherein said cocking includes compressing the spring between the drive member and the actuation member with the motor at least until the cocking flange engages the cocking arms to hold the spring in the cocked state, and wherein said firing includes releasing the spring by driving one or more arm engagement surfaces of the drive member with the motor to release the cocking flange from the cocking arms.

\* \* \* \* \*